(12) United States Patent
Maschhoff et al.

(10) Patent No.: US 10,444,145 B2
(45) Date of Patent: Oct. 15, 2019

(54) HYPERSPECTRAL INFRARED SOUNDERS DEPLOYABLE AS A CONSTELLATION FOR LOW ORBIT MWIR ATMOSPHERIC MEASUREMENTS

(71) Applicant: BAE Systems Information and Electronic Systems Integration Inc., Nashua, NH (US)

(72) Inventors: Kevin R. Maschhoff, Wakefield, MA (US); Gerard M. Perron, Acton, MA (US); John J. Polizotti, Pittsfield, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 34 days.

(21) Appl. No.: 15/571,197

(22) PCT Filed: May 3, 2016

(86) PCT No.: PCT/US2016/030546
§ 371 (c)(1),
(2) Date: Nov. 1, 2017

(87) PCT Pub. No.: WO2016/179161
PCT Pub. Date: Nov. 10, 2016

(65) Prior Publication Data
US 2019/0154576 A1 May 23, 2019

Related U.S. Application Data

(60) Provisional application No. 62/156,517, filed on May 4, 2015.

(51) Int. Cl.
*G01J 3/02* (2006.01)
*G01N 21/41* (2006.01)
(Continued)

(52) U.S. Cl.
CPC ............. *G01N 21/41* (2013.01); *G01J 3/18* (2013.01); *G01J 3/2823* (2013.01); *G01J 5/007* (2013.01);
(Continued)

(58) Field of Classification Search
CPC .. G01J 3/18; G01J 3/2823; G01J 5/007; G01J 5/20; G01N 2021/1793; G01N 2021/3531; G01N 21/41; H01L 31/107
See application file for complete search history.

(56) References Cited

U.S. PATENT DOCUMENTS 6,222,187 B1 4/2001 Shivanandan
6,246,132 B1 6/2001 Joshi et al.
(Continued)

OTHER PUBLICATIONS

International Search Report, PCT/US2016/030546, dated Aug. 4, 2016, 8 pages.
(Continued)

*Primary Examiner* — Marcus H Taningco
(74) *Attorney, Agent, or Firm* — Maine Cernota & Rardin; Scott J. Asmus (57) ABSTRACT

A mid-wave infrared system provides high spatial and temporal resolution measurements of atmospheric temperatures and moisture fields using a constellation of low earth orbit satellites. The disclosed system is smaller, lighter, less complex, and requires less energy than existing systems, due to implementation of an infrared avalanche photodiode array detector that provides enhanced sensitivity with reduced cooling requirements, and an Offner spectrometer having a novel a refractive element inserted near the grating that reduces the size and power requirements of the spectrometer. Embodiments of the disclosed method include deploying a constellation of devices for cooperative infrared sensing of atmospheric phenomena at similar rates, lower cost, and much higher resolution compared to geosynchronous
(Continued)

approaches. Some embodiments further include combined analysis of measurements obtained by the disclosed devices with complementary measurements made by other low-earth and high-earth orbital and/or ground-based devices.

17 Claims, 9 Drawing Sheets

(51) Int. Cl.
| | |
|---|---|
| *G01N 21/3518* | (2014.01) |
| *G01W 1/04* | (2006.01) |
| *G01J 3/18* | (2006.01) |
| *G01J 3/28* | (2006.01) |
| *G01J 5/00* | (2006.01) |
| *G01J 5/20* | (2006.01) |
| *H01L 31/107* | (2006.01) |
| *G01J 5/04* | (2006.01) |
| *G01J 5/02* | (2006.01) |
| *G01J 5/06* | (2006.01) |
| G01N 21/3554 | (2014.01) |
| G01N 21/17 | (2006.01) |
| G01N 21/3504 | (2014.01) |

(52) U.S. Cl.
CPC .............. *G01J 5/0205* (2013.01); *G01J 5/041* (2013.01); *G01J 5/061* (2013.01); *G01J 5/20* (2013.01); *G01N 21/3518* (2013.01); *G01W 1/04* (2013.01); *H01L 31/107* (2013.01); *G01J 2005/202* (2013.01); *G01N 21/3554* (2013.01); *G01N 2021/1793* (2013.01); *G01N 2021/3531* (2013.01)

(56) References Cited

U.S. PATENT DOCUMENTS

| | | | |
|---|---|---|---|
| 6,634,600 B2 | 10/2003 | Krawczyk et al. | |
| 8,390,806 B1 | 3/2013 | Subramanian | |
| 8,866,322 B2 | 10/2014 | Tchoryk, Jr. et al. | |
| 8,908,178 B1 | 12/2014 | Hanson et al. | |
| 2006/0038128 A1* | 2/2006 | D'Souza | G01J 3/2803 250/332 |
| 2009/0018801 A1* | 1/2009 | Gladkova | H03M 7/3082 703/2 |
| 2012/0050750 A1 | 3/2012 | Hays et al. | |
| 2012/0194822 A1 | 8/2012 | Buijs | |
| 2013/0179078 A1* | 7/2013 | Griffon | G06Q 50/26 702/3 |
| 2014/0375898 A1 | 12/2014 | Kurozuka et al. | |

OTHER PUBLICATIONS

Li et al., "Advanced baseline sounder (ABS) for future geostationary operational environmental satellites (GOES-R and beyond)", Proc. SPIE 4895, Applications with Weather Satellites, (Jun. 16, 2003); doi: 10.1117/12.466506.
Pagano et al., "Concept for a low cost MWIR Imaging Sounder for Low Earth Orbit", American Meteorological Society 2013.
Pagano, "Matching observations to model resolution for future weather and climate applications", Proc. SPIE 6966, Algorithms and Technologies for Multispectral, Hyperspectral, and Ultraspectral Imagery XIV, 69660Z (Apr. 11, 2008); doi: 10.1117/12.777611. Orlando, FL.
Krijger et al., "The effect of sensor resolution on the number of cloud-free observations from space", Atmospheric Chemistry and Physics Discussions, European Geosciences Union, 2006, 6 (3), pp. 4465-4494. <hal-00301415>.
Solomon et al., "Climate Change 2007—The Physical Science Basis", Contribution of Working Group I to the Fourth Assessment Report of the IPCC. Cambridge University Press.
Zavodsky et al., "The impact of atmospheric infrared sounder (AIRS) profiles on short-term weather forecasts", Proc. SPIE 6565, Algorithms and Technologies for Multispectral, Hyperspectral, and Ultraspectral Imagery XIII, 65651J (May 16, 2007); doi: 10.1117/12.718121. Orlando, FL.
http://tes.jpl.nasa.gov/mission/biomassburning.
National Research Council 2007. "Earth Science and Applications from Space: National Imperatives for the Next Decade and Beyond". Washington, DC: The National Academies Press. https://doi.org/10.17226/11820.

* cited by examiner

HYPERSPECTRAL INFRARED SOUNDERS DEPLOYABLE AS A CONSTELLATION FOR LOW ORBIT MWIR ATMOSPHERIC MEASUREMENTS

CROSS-REFERENCE TO RELATED APPLICATIONS

This application claims the benefit of U.S. Provisional Patent Application No. 62/156,517, filed on May 4, 2015, which is herein incorporated by reference in its entirety.

FIELD OF THE DISCLOSURE

The following disclosure relates generally to earth science measurements, and more particularly to atmospheric measurements for the purpose of weather forecasting by means of infrared soundings.

BACKGROUND

For more than a decade, spectral radiance data obtained from airborne and orbital platforms has been used to quantify the 3-dimensional special and temporal variability of atmospheric temperature and moisture fields, so as to understand and predict the development of extreme weather events. In particular, data from the Atmospheric Infra-Red Sounder ("AIRS") on the NASA Aqua spacecraft have been routinely used for this purpose.

Assimilation of AIRS radiances in channels which support the derivation of high vertical resolution moisture and temperature field measurements and similar measurements, for example by the EUMETSAT/IASI (EUropean organisation for the exploitation of METeorological SATellites/Infrared Atmospheric Sounding Interferometer), have had a greater impact on the accuracy of medium-range numerical weather forecasts than that of any other single instrument. However, their LEO orbits ("Low Earth Orbits") allows at most two observations per day per platform, which limits the ability to comprehensively sample rapidly changing atmospheric fields.

The NASA/NOAA GOES-R HES ("Geostationary Operational Environmental Satellite R-series Hyperspectral Environment Suite") program sought to provide this high vertical resolution capability in geostationary orbit, which has been the traditional choice for high resolution temporal frequency measurements. However, HES has been deferred indefinitely following the formulation phase due to the expected high cost and high risk of cost growth in the development of a geosynchronous implementation. In particular, attaining finer spatial resolution observations of these atmospheric fields, for example resolutions in the range of 1-3 km, would be very challenging and costly to obtain from geosynchronous orbit.

In order to better understand the initiation and development of extreme weather events, the spatial resolution and temporal refresh rate of measurements of the atmospheric temperature and moisture fields and their dynamics must be substantially improved.

Numerous studies illustrating the substantial potential for weather forecast improvements due to rapidly refreshed high spectral resolution infrared spectral sounding measurements were performed in advance of, and during the GOES-R HES Formulation Phase. In general, these benefits are the result of comparative measurements that show the development of unstable atmospheric conditions or that reveal motion of the atmosphere at different altitudes.

Figure 1A:
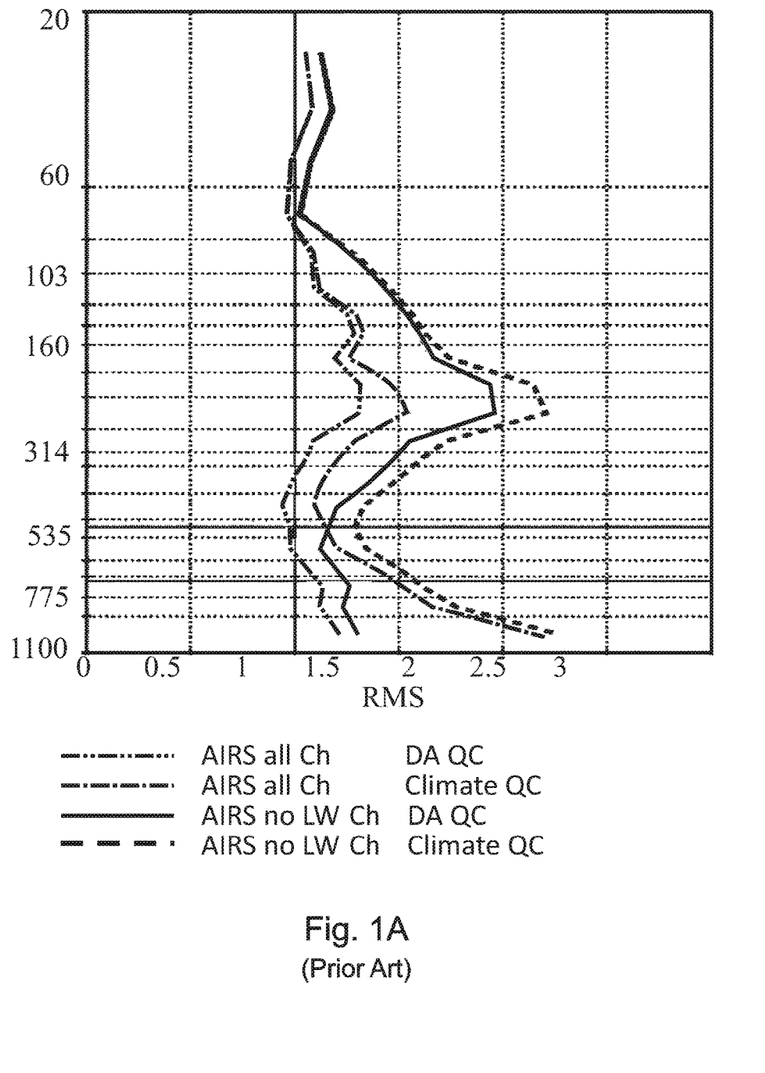
FIG. 1A is a graph showing AIRS Vertical Temperature Profile Accuracy with Different Spectral Channel Sets.

Recent analysis by members of the NASA AIRS Science Team shows that observations in the spectral range 1950-2450 cm-1 at AIRS' spectral resolution, result in vertical temperature profile retrieval accuracy in the lower troposphere nearly as good as that derived using the full AIRS spectral channel set. FIG. 1A is a graph of AIRS/AMSU retrievals global cases for Jul. 10, 2012. It shows RMS differences from ECMWF "truth" of Quality Controlled (QC'd) AIRS/AMSU temperature profile retrievals obtained when using all AIRS channels and when using all but 15 μm or 11 μm AIRS bands. Results are shown using two QC procedures: data assimilation QC, which accepts fewer but more accurate retrievals, and climate QC, which accepts many more retrievals derived under more difficult cloud conditions. Results obtained using only mid-shortwave channels is somewhat degraded from those using all AIRS channels, but are still very good using either QC procedure. While these studies included concurrent use of AMSU observations, results obtained using all MWIR AIRS observations, but without using any AMSU observations, are similar.

Weather and climate processes are intimately linked by water vapor. Accurate knowledge of the distribution of water held in the atmosphere is therefore indispensable to predicting the amount, time, and location of precipitation. Recent studies by the National Research Council (NRC) and the Intergovernmental Panel on Climate Change (IPCC) showed that the Earth's climate can undergo changes in response to increasing concentrations of other greenhouse gases and aerosols, and that these changes may profoundly affect atmospheric water vapor, clouds, and precipitation patterns. Observation of changes in the distribution and dynamic behavior of water vapor in the coming years would further quantify the relationship between greenhouse gas concentrations and environmental phenomena with the greatest impact on human society, ranging from drought to severe storms, and would improve our ability to forecast the impact of these changes in the most policy-relevant terms. High-frequency measurements are especially important for characterizing these relationships and noting potential changes in dynamic weather events and/or diurnal convective processes. Recently, the assimilation of AIRS radiances into a regional atmospheric model has shown to improve the accuracy of precipitation likelihood predictions.

Figure 2:
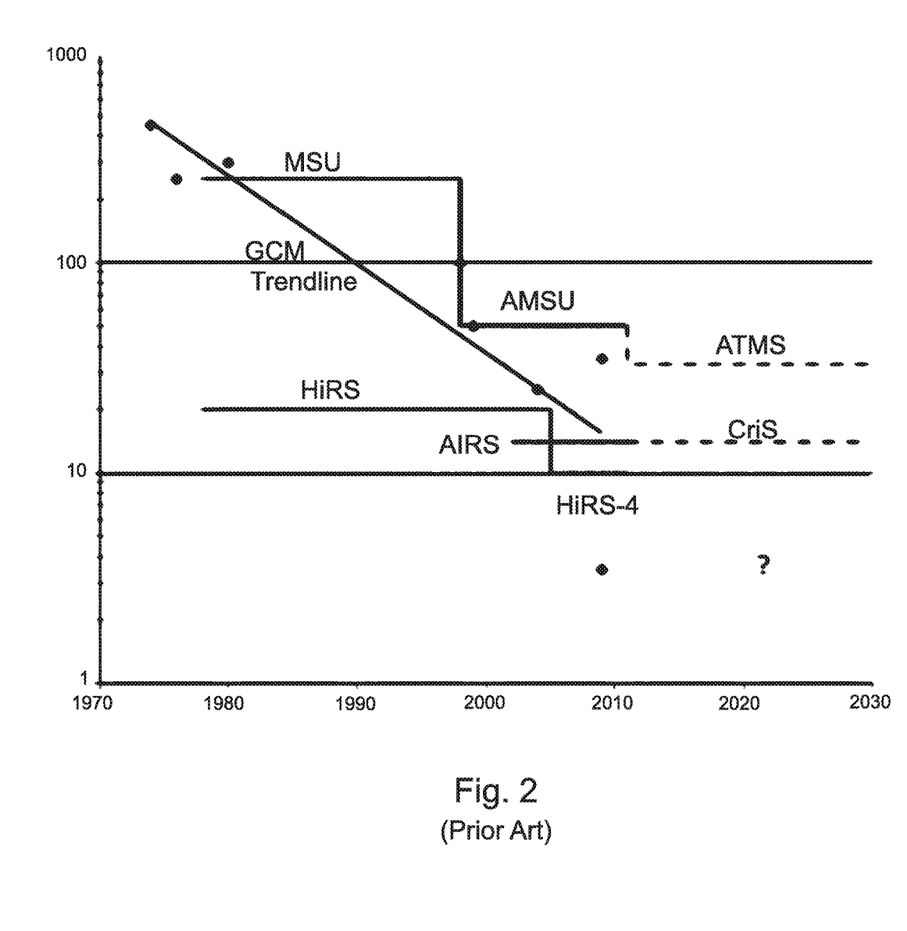
FIG. 2 is a graph showing improvements in GCM modeling and IR and $\mu$-wave weather and climate instrument resolutions that predict the need for horizontal resolution observations at the 1-2 km scale in the next 2 decades.

Cloud-resolving models under development today will likely form the basis for the next generation of weather and climate models. FIG. 2 shows improvements in GCM resolution compared to infrared and microwave observations over the past three decades. The trend line projects that operational models will be operating at horizontal spatial resolutions of 2-3 km within the next decade. Regional high resolution models are already being used operationally. Prior work also demonstrates that validation of a model of a given resolution must have observations as good as, or better than, the model itself, in order to minimize errors due to Nyquist spatial filtering processes in the models.

Unfortunately, the horizontal resolutions of current IASI and JPSS systems are coarser than 10 km, and the horizontal resolutions of the microwave and GPS-RO soundings are many 10's of km.

The societal value of fundamental measurements of the atmosphere, including the vertical temperature and moisture profiles and related characteristics, have long been recognized (See GOES-R HES discussion and Weather Panel Report Section) for their value in ongoing fundamental research, for the supporting data they provide for new research missions, and their value for operational earth observations for weather forecasting and other applications. However, the large programmatic failures of NPOESS and large disruptions to the GOES-R program are traceable in part to the spiraling complexity and cost associated with development of large instruments and multi-payload platforms such as NPOESS and GOES-R. NASA and other space agencies are exploring the use of distributed observing system architectures for various environmental observations.

The driving technical challenges on this path arise from the need to provide observations of the required data quality while fitting within the severe payload accommodation constraints of an economically favorable distributed architecture. Unfortunately, high spectral resolution payloads are typically large, heavy, and complex, and require large amounts of electrical power, especially for cooling. As a consequence, such instrument systems are expensive, and difficult to accommodate on space and airborne platforms, limiting their use.

A need, therefore, exists for a smaller, lighter, less complex, more energy efficient system for high spatial and temporal resolution measurement of atmospheric temperatures and moisture fields and their dynamics.

SUMMARY

A novel midwave infra-red system and method for high spatial and temporal resolution measurement from low earth orbit of atmospheric temperatures and moisture fields and their dynamics is smaller, lighter, less complex, and requires less energy than existing systems. The disclosed invention is referred to herein as "MISTiC," which is an acronym for Midwave Infrared Sounding of Temperature and humidity in a Constellation. While the last letter in this pneumonic is taken from the word "constellation," note that the term "MISTiC" is sometimes used herein to refer to the disclosed device in the singular, and that the term "MISTiC constellation" is sometimes used to unambiguously refer to a plurality of such devices operating in a cooperative manner.

Embodiments of the disclosed system exploit contemporary technology, including infrared avalanche photodiode arrays ("APD's") and high-efficiency methods for cooling infrared spectrometers and detectors, to miniaturize overall payload size, mass, and power. In some embodiments, these improvements lead to increases in system sensitivity performance, while in other embodiments they provide the same or even somewhat degraded sensitivity as compared to prior art systems, but with substantial reductions in size, mass, and power requirements at the instrument payload level.

In some embodiments, an APD array that can be operated at much higher operating temperatures is combined with a spectrometer that has an architecture similar to an Offner spectrometer, but includes a novel a refractive element inserted near the grating to reduce the size of the spectrometer while retaining the low-emissivity benefits of the Offner design. The overall size reduction attained by these embodiments enables the MISTiC devices to be more easily deployed, and to be installed on a much broader range of orbiting host platforms, including distributed architectures.

Embodiments of the disclosed method include deployment of a constellation of MISTiC devices for cooperative infrared sensing of atmospheric phenomena. Some method embodiments further include the combined analysis of infrared measurements obtained by MISTiC devices and complementary measurements made by other low-earth and high-earth orbital and/or ground-based devices.

Embodiments of the present invention include the following:

Embodiment 1

A device suitable for making infrared atmospheric measurements, the device comprising:
an avalanche infrared photodiode array;
a cryo-cooler configured to cool the photodiode array;
a spectrometer having an Offner architecture, said spectrometer including a grating and a refractive element proximal to the grating;
an optical and self-emission baffle; and
a two-zone passive thermal radiator having a first zone configured to cool the baffle while in orbit and a second zone configured to cool the spectrometer while in orbit.

Embodiment 2

The device of embodiment 1, wherein the cryo-cooler is configured to cool the photodiode array to a temperature that is between 75K and 100K.

Embodiment 3

The device of embodiment 2, wherein the cryo-cooler is able to cool the photodiode to a temperature below 100K while consuming less than 15 W of power.

Embodiment 4

The device of any preceding embodiment, wherein the cryo-cooler is an NGST miniature pulse-tube cooler that has a specific cooling power of at least 20 W/W at 100K.

Embodiment 5

The device of any preceding embodiment, wherein the first zone of the two-zone radiator is able to cool the baffle to a temperature that is between 175K and 195K.

Embodiment 6

The device of any preceding embodiment, wherein the spectrometer is limited to detecting infrared radiation in the range of 1950 $cm^{-1}$ to 2450 $cm^{-1}$.

Embodiment 7

The device of any preceding embodiment, wherein the spectrometer is configured to detect water vapor absorption lines in the range of 1950-2325 $cm^{-1}$.

Embodiment 8

The device of any preceding embodiment, wherein the spectrometer has a minimum resolution of less than 2.3 $cm^{-1}$.

Embodiment 9

The device of any preceding embodiment, wherein the spectrometer has a radiometric sensitivity threshold of less than 200 mK.

Embodiment 10

The device of any preceding embodiment, wherein the device has a total weight of less than 12 kg.

Embodiment 11

The device of any preceding embodiment, wherein the device has a total power consumption requirement of less than 40 W.

Embodiment 12

The device of any preceding embodiment, further comprising an on-board spectral data handling system that employs an FPGA-based processing chain.

Embodiment 13

A method of making hyperspectral soundings of the earth's atmosphere from a constellation of earth satellites, the method comprising:
deploying a plurality of satellites in a constellation of orbits surrounding the earth, wherein a device as described in embodiment 1 is included with each of the satellites; and
obtaining from the devices cooperative distributed infrared sensing measurements of atmospheric phenomena.

Embodiment 14

The method of embodiment 13, wherein the satellites are deployed in low earth orbit at an altitude of approximately 705 km above the earth's surface.

Embodiment 15

The method of embodiment 13 or 14, wherein the constellation is able to make observations of a region that are repeated every 90 minutes.

Embodiment 16

The method of embodiment 13, 14, or 15 wherein the constellation is able to make repeated observations of a region with a repetition interval of less than fifteen minutes.

Embodiment 17

The method of any of embodiments 13-16, wherein observations obtained from the constellation are provided together with observations obtained from other devices as input for at least one of atmospheric modeling and weather forecasting.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the inventive subject matter.

BRIEF DESCRIPTION OF THE DRAWINGS

The invention is further described with reference to the accompanying drawings, wherein.

These and other features of the present embodiments will be understood better by reading the following detailed description, taken together with the figures herein described. The accompanying drawings are not intended to be drawn to scale. For purposes of clarity, not every component may be labeled in every drawing.

DETAILED DESCRIPTION

A midwave infra-red system for high spatial and temporal resolution measurement from orbit of atmospheric temperatures and moisture fields and their dynamics is disclosed that is smaller, lighter, less complex and requires less energy than existing systems. The disclosed invention is referred to herein as "MISTiC," which is an acronym for Midwave Infrared Sounding of Temperature and humidity in a Constellation. While the last letter in this pneumonic is taken from the word "constellation," note that the term "MISTiC" is sometimes used herein to refer to the disclosed device in the singular, and that the term "MISTiC constellation" is sometimes used to unambiguously refer to a plurality of such devices operating in a cooperative manner.

1.0 Applicability to Earth Science Measurements

Embodiments of the disclosed system utilize improvements in technology, in infrared sounding methodology, and in the use of distributed measurements from a low earth orbit ("LEO") "constellation" of platforms, so as to provide atmospheric observations at the higher re-fresh rates and finer spatial resolutions that are needed for improved observation and prediction of the initiation and development of dynamic weather events at significantly lower costs than previously available or proposed geosynchronous approaches. Specifically, embodiments make distributed measurements using a "constellation" of low earth orbiting satellites so as to provide the high temporal refresh capabilities that are more typically associated with a geosynchronous approach, such as GOES-R HES, in combination with the high spatial resolution that is more easily obtained from low earth orbit.

Weather Forecast Improvement Via More Frequent, Finer Infrared Sounding

In embodiments, a "constellation" of MISTiC devices can be used in a system-of-systems approach to monitor the atmosphere from low earth orbit. In some of these embodiments, MISTiC's high spatial and temporal resolution observations of the troposphere are combined with high spectral resolution but coarser spatial resolution infrared measurements that can be obtained from existing infra-red and microwave sounding constellations, thereby providing an unprecedented, dynamic view of the atmosphere.

Figure 1B:
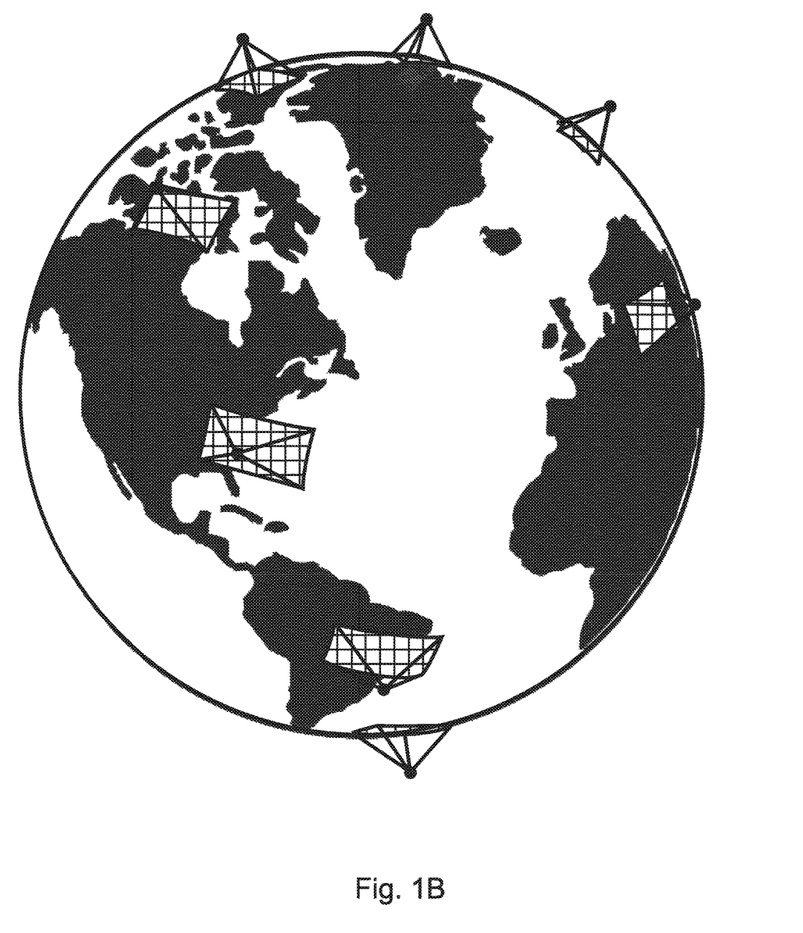
FIG. 1B is a view of earth showing a MISTiC Temperature and Humidity Sounding Constellation that can provides observations of the same area every 90 minutes.
Figure 1C:
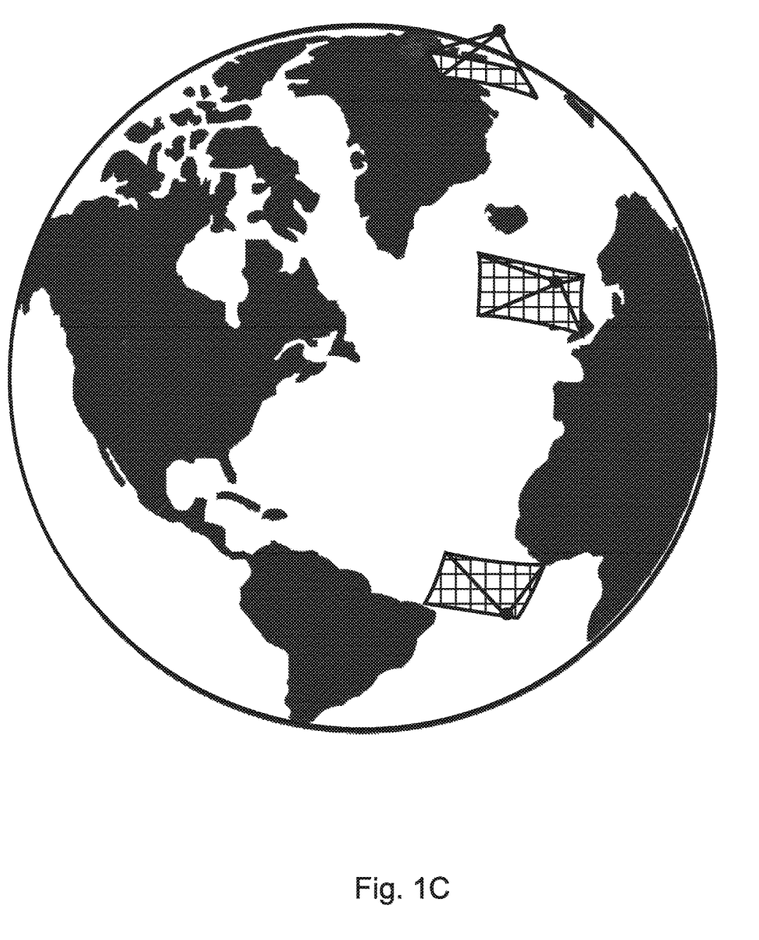
FIG. 1C is a view of earth showing a MISTiC Temperature and Humidity Sounding Constellation that can provide three observations of a region with a delay between observations of a few minutes

By restricting the spectral coverage to MWIR channels, and by using a series of observations from a constellation of microsatellites hosting small IR sounding spectrometer payloads, embodiments of the disclosed system can affordably provide observations at, or approaching, the refresh rates possible from geosynchronous systems. For example, the MISTiC constellation shown in FIG. 1B can provide observations of the same area every 90 minutes, while the constellation shown in FIG. 1C can provide three observations of a region with a separation of a few minutes to support observation of vertically resolved motion vector winds. Altogether, these constellations can provide MWIR measurements of the troposphere (especially the lower troposphere and boundary layer) prior to cloud formation that are sufficient for weather models to predict where new storms will develop, and at an observation tempo that can make it much more likely that conditions for storm development will be witnessed by the observing system.

In embodiments, a MISTiC constellation can provide observations in low earth orbit that are sufficient to monitor the more slowly changing and spatially more uniform upper troposphere and lower stratosphere, both in clear fields (IR-sounders), and/or cloudy fields (microwave sounders, and GPS-RO). It is further anticipated that once the GOES-R series Advanced Baseline Imagers are introduced over the US, along with comparable meteorological imaging capability provided by EUMETSAT, it will be possible to use the high spatial resolution/rapid refresh data from those imagers together with data from embodiments of the disclosed MISTiC system to ensure accurate identification of partially cloudy MISTiC sounding fields of view, and to provide cloud phase information that MISTiC alone may not be able to obtain.

The increased observation density of embodiments of the disclosed MISTiC system enables data obtained therefrom is able to meet the information needs of the next generation of general circulation models ("GCM's"), such that assimilated MISTiC data will be able to provide a primary constraint on the fine-scale atmospheric structure forecasts of future regional and meso-scale numerical weather models.

In embodiments, the higher spatial resolution of MISTiC also results in a higher fraction of cloud-free scenes and a greater likelihood of obtaining cloud-free observations. Analyses with AIRS and MODIS data demonstrate that the increase in spatial resolution from 13.5 km for AIRS to 2-3 km provided by embodiments of MISTiC results in an approximate factor of 2 improvement in cloud-free fractional yield, and a significant increase in the number of cloud-free soundings. Currently, only cloud-free radiances from AIRS and IASI are assimilated operationally in weather models. Also, MWIR radiance observations are not currently assimilated because of perceived problems resulting from effects of non-Local Thermodynamic Equilibrium (non-LTE), and solar radiation reflected by clouds and the surface, on these channels. These factors are already accounted for in the AIRS Science Team retrieval methodology, and can be easily accounted for as well in the radiance assimilations models.

Furthermore, the improvements in both spatial and temporal sampling densities provided in embodiments of the disclosed MISTiC system improve the ability to characterize the distribution of water held in the atmosphere, and the relationships between greenhouse gas concentrations and environmental phenomena, and to note potential changes in dynamic weather events or diurnal convective processes.

3D-Winds with Simultaneous Atmospheric State Observation-Together with Pollution Transport Pathway Studies Infrared sounders of the current generation have proven valuable in understanding the processes affecting water vapor transport and cloud formation in the atmosphere over somewhat longer time-scales. The new capabilities provided by embodiments of the disclosed MISTiC system can provide a powerful constraint on global circulation models (GCMs) by simultaneously observing both its current state and its rate of change with high spatial and vertical resolution. For example, in the embodiment of FIG. 1C, several infrared spectral soundings with high spatial and vertical resolution observed over a given region by 3 MISTiC microsatellites flying in formation can provide a triplet of observations that can be used to measure both cloud and moisture motion-vector winds (CMMV and MMVW) at different pressure altitudes, and with an approximate vertical resolution of 50 mb through the troposphere.

Figure 3:
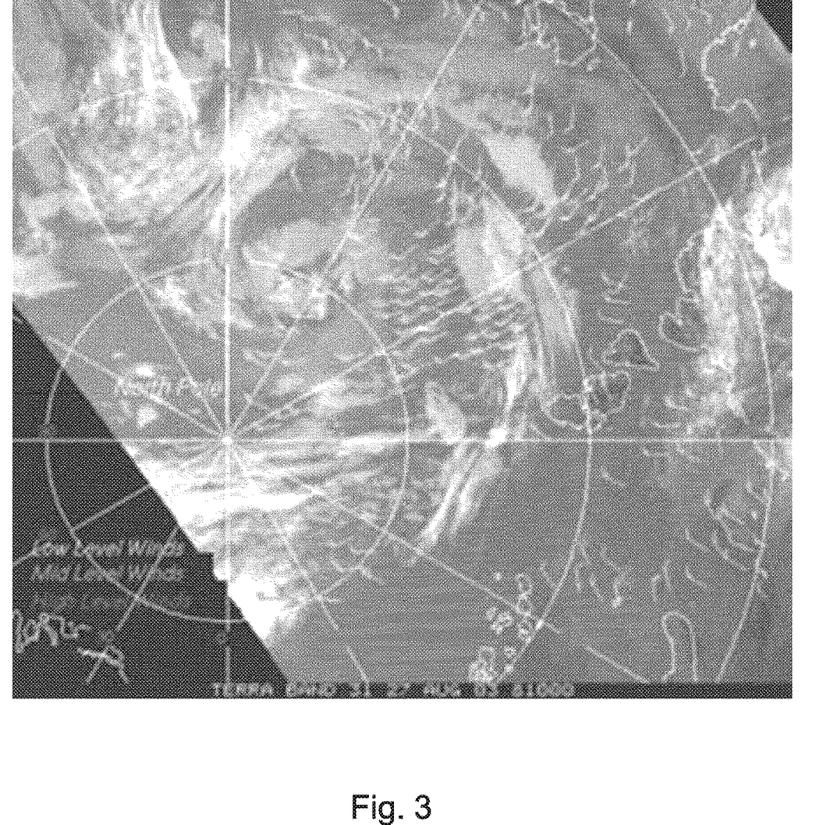
FIG. 3 is an image illustrating motion-vector winds derived from MODIS constellation observations.
Figure 4:
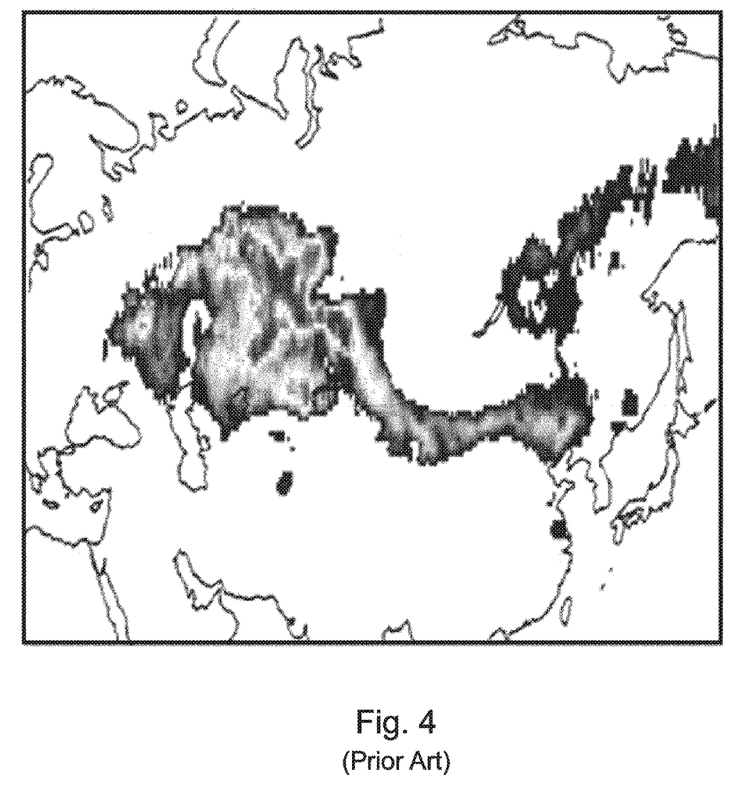
FIG. 4 is an image illustrating a hyperspectral observation of CO by the AIRS hyperspectral sounder.

Also, each of these observations can provides near AIRS-quality vertical profiles of temperature and moisture, (atmospheric state) for the same atmospheric column. In a similar embodiment, a constellation of 12 micro-satellites, comprising 4 orbital planes, each plane including a three-satellite formation, can provide vertically resolved tropospheric wind and atmospheric state measurements globally every 3 hours. These observations can have an unprecedented impact on short-term numerical weather forecasting. FIG. 3 is an image illustrating motion-vector winds derived from MODIS constellation observation. Embodiments of MISTiC can provide higher vertical resolution of winds than MODIS (which uses multi-spectral observations), due to the use of hyperspectral sounding In addition to these weather forecast-oriented improvements, embodiments of MISTiC can fundamentally improve pollution transport research. With reference to FIG. 4, which presents a map of Russian wildfires, AIRS CO (ppbV) dated Aug. 12, 2016, simultaneous observations by TES of CO together with other constituents of air pollution indicate that CO can be used as a tracer species, and suggests its use in transport studies. Embodiments of the MISTiC system can observe CO (carbon monoxide) at higher spatial resolution using hyperspectral methods like AIRS, and can illuminate pollution transport pathways by revealing motion through a sequence of more frequent observations. The MISTiC spectral range in some embodiments captures strong absorption/emission bands of both CO and $N_2O$, allowing these species to be observed in a vertically resolved fashion. This transport observation capability can be highly complementary to observations planned for GACM, ASCENDS and PACE, and can provide a fundamental tool for understanding atmospheric transport mechanisms and processes.

2.0 Description of MISTiC Technology

General Approach

The size, weight, complexity, and electrical requirements of the disclosed high spatial and temporal resolution mid-wave infra-red MISTiC system are reduced by combining a novel, compact spectrometer design that incorporates the power efficiencies of the Offner architecture with an avalanche photodiode array that can be operated at relatively higher temperatures, so that the sizes and weights of the power supply and cryo-cooler are also significantly reduced, thereby allowing the disclosed system to provide enhanced spectral radiance data quality within the resource constraints of a micro-satellite.

Technical Approach for the Instrument

A four-fold approach is incorporated into embodiments of the invention, as follows:

A dramatically reduced spectral range is employed using spectral channels that place the lowest thermal demands on the payload while providing the greatest vertical resolution.

A new MWIR FPA technology based on avalanche photodiodes is employed, whose intrinsic photo-signal gain and low noise figure allow much higher detector operating temperature.

A novel cooled infrared spectrometer is employed whose opto-mechanical and thermal design presents the least thermal load and requires the least platform resources.

Spectral bands within a system-of-systems context are selected to avoid replication of observation capability in the disclosed MISTiC system that exist elsewhere in the system of systems.

Embodiments of the MISTIC system use just the 1950-2450 cm-1 range, which includes the region dominated by $CO_2$ absorption, and successfully addresses the challenges posed by solar reflectance contamination effects and non-local thermal equilibrium effects when deriving the level-2 vertical temperature profile product from channels in this range. Additionally, embodiments use water vapor absorption lines in the 1950-2325 cm-1 range rather than the (effectively equivalent) 1333-1660 $cm^{-1}$ range used by some prior art systems, thereby enabling a consolidated MWIR spectral band to be used for measuring $CO_2$ and $H_2O$ in a single spectrometer.

Key instrument characteristics in embodiments are shown in Table 1.

TABLE 1

| MISTiC Instrument Performance Characteristics | | |
|---|---|---|
| Characteristic | Value | Comments |
| Minimum Spectral Frequency | 1950 $cm^{-1}$ | 5.128 μm |
| Maximum Spectral Frequency | 2450 $cm^{-1}$ | 4.082 μm |
| Spectral Sampling | 2.1 nm/sample | Apx. 500 spectral samples |
| Spectral Resolution @ minimum | 1.7 $cm^{-1}$ | Resolves Multiple H2O Lines |
| Spectral Resolution @ maximum | 2.3 $cm^{-1}$ | Comparable to AIRS |
| Spectral Calibration Knowledge | 1/100,000 | $\delta\lambda/\lambda$ |
| Angular Sampling | 1.64 mr (cross-dispersed) | 1.15 km (@ Nadir) |
| Orbital Altitude and Orbit | 705.3 km | Polar/Sun-Synchronous |
| Angular Range | 1570 radians | 90 Degrees-Same as AIRS |
| Spatial Resolution | <3 km (geometric mean) | @ Nadir |
| Radiometric Sensitivity | <200 mK | (<150 mK @ 4166 cm-1) |
| Radiometric Accuracy | <1% | @ 300K Scene Background |
| Anticipated Level-2 Data Product Characteristics, for Primary Data Products | | |
| Vertical Temperature Resolution | Apx. 1 km | Lower Troposphere |
| Layer Accuracy | Apx. 1.25K | Lower Troposphere |
| Vertical Humidity Resolution | Apx. 2 km | Lower Troposphere |
| Layer Humidity Accuracy | Apx. 15% | Lower Troposphere |

The second key attribute of the disclosed system is that the baselined IRFPA (infra-red focal planar array) operates at an elevated temperature relative to prior art systems operating at the same resolution, for the expressed purpose of reducing the required active cooling power. In embodiments, the IRPFA is composed of a 640×480 HgCdTe Avalanche Photo-Diode (APD) detector array and a CMOS ROIC. This type of detector actually uses a Cd mole fraction, which gives it a MWIR band gap, such that its electronic band structure supports an avalanche gain of more than 100× at a noise figure less than 1.4.

Figure 5:
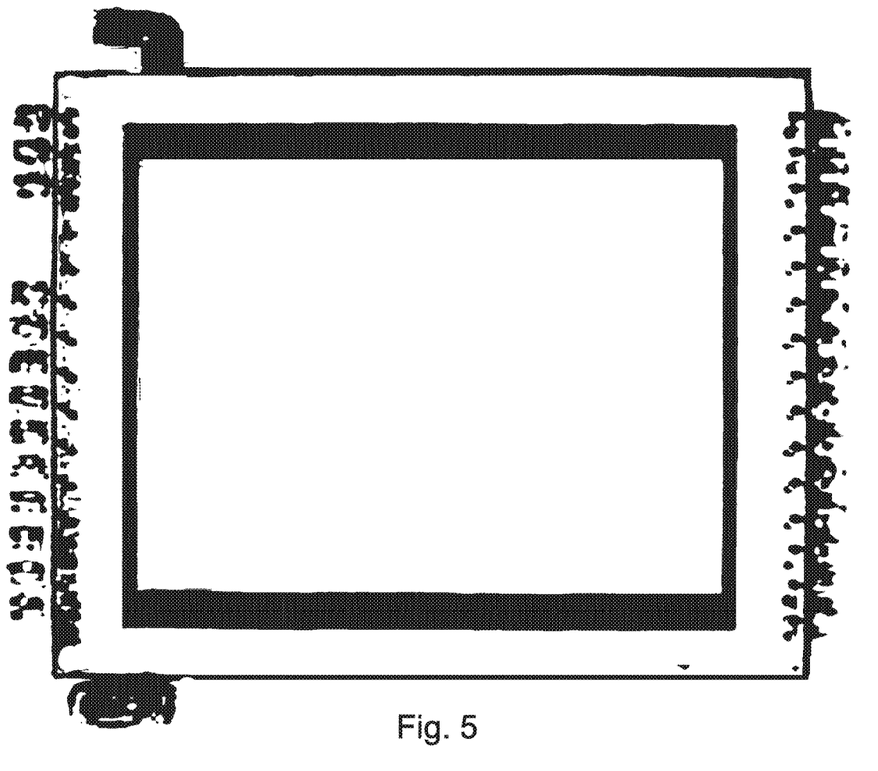
FIG. 5 is an image of a MWIR (mid-wave infra-red) HgCdTe avalanche photodiode-based IR focal plane array detector included in an embodiment.

In embodiments, the IRFPA can be operated at a temperature as high as 100K, which is 25 K higher than an IRFPA that does not employ photo-signal gain. Certain embodiments employ an NGST miniature pulse-tube cooler that has a specific cooling power of approximately 20 W/W at 100K, which is 1.8× better than the 36 W/W needed at approximately 75K (or lower) for some prior art systems. FIG. 5 presents an illustration of an IRFPA that is able to provide the type of high-sensitivity hyperspectral measurements that are especially needed for monitoring the weak emissions from $CO_2$ in the upper troposphere, while operating at a relatively warm temperature of about 100K. In embodiments, such warm temperature operation minimizes the load placed on the cryo-cooler, allowing the cryo-cooler to operate in a much more efficient range, in a so-called "virtuous cycle."

In embodiments, the total load (active FPA and passive conductive and radiative loads) on the cryo-cooler cold-tip is approximately 750 mW at 100K, leading to a total cryo-cooler power of about 15 W, which is approximately 10× lower than some prior art systems.

Figure 6:
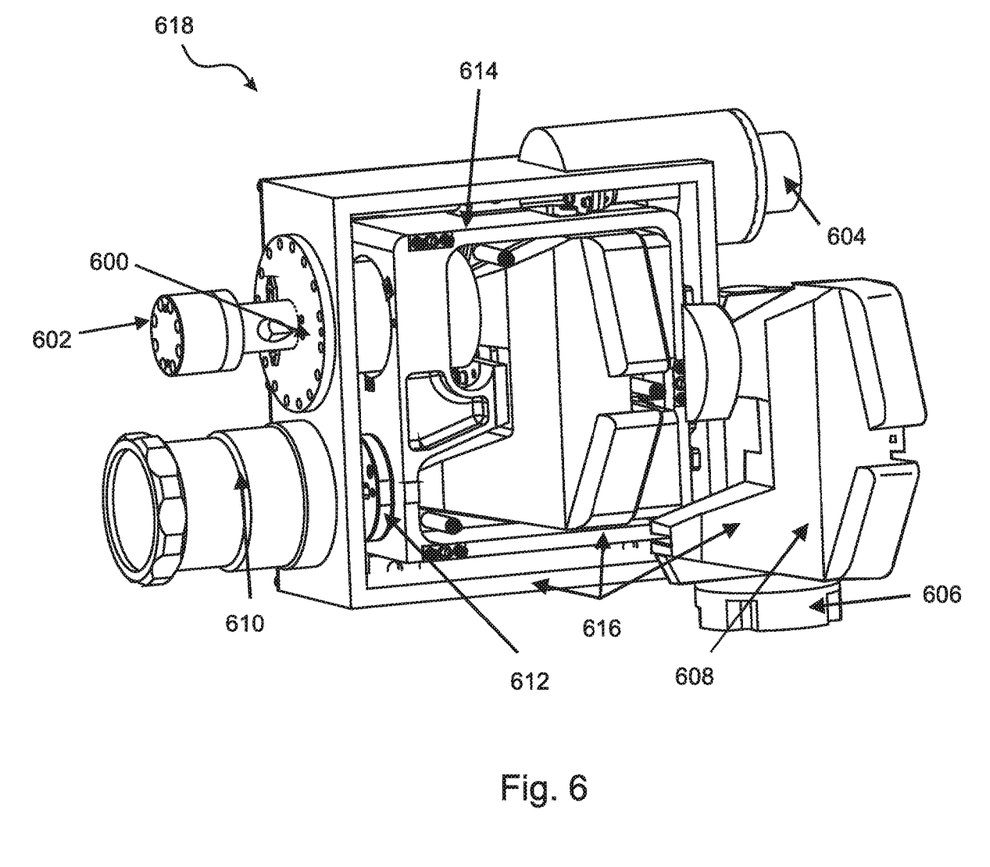
FIG. 6 is a perspective view drawn to scale of a miniature, cooled spectrometer, shown with the baffle and cover pulled away to reveal the interior optics, that is simultaneously optimized for high operating temperature, high throughput, and low self-emission.

The third key attribute of the disclosed MISTiC system that minimizes the thermal accommodation requirements is that it employs a novel spectrometer opto-mechanical and thermal design that minimizes the total thermal load and maximizes the temperature at which that load is presented. FIG. 6 shows a diagram of the spectrometer 618 in an embodiment that incorporates a specialized Offner design having a low-mass electro-formed baffle that is cooled to 195K by a small, passive radiator, while the rest of the optics are warmer.

The specific embodiments illustrated in FIG. 6 includes 500 spectral channels, 480 spatial channels, and 2.2 nm/pixel, 25 um pixels. Features of the spectrometer indicated in the figure include:

Item Number Feature

600 Detector Dewar FPA (100K)

602 Detector Dewar (Thermal Link)

604 Cold Shield Thermal I/F

606 Pulse Tube μ-Cooler Assembly

608 Cold Thermal Baffle (195K) Black Interior/Gold Exterior

610 Spectrometer Fore Optics, F#/3, appx. 15 mm Focal Length

612 Slit Block

614 Aluminum Optics/Grating/Housing appx. 200K

616 MLI

Characteristics of the embodiment illustrated in FIG. 6 are listed in Table 2 below, where they are compared with a small Dyson-class spectrometer having the same spectral range and resolution. Note the overall reduction in size, mass, and power.

TABLE 2

Comparison of MWIR Spectrometer Implementations in a modified Offner-type embodiment with a Dyson-type instrument

| Dispersion Device Characteristics | Instrument Implications | Primarily Reflective (Mod. Offner-Type) with Electro-formed Baffle | Primarily Refractive (Dyson Type) |
| --- | --- | --- | --- |
| Optical Throughput Efficiency | Higher Throughput→ Higher Detector Temp (Low Power) | 99% | 75% |
| Exposed Aft-Optics Solid Angle (after dispersion) | Lower solid angle→ higher temp. (Smaller Cryo-rad.) | About 0.3 str | About 1 str |
| Spectrometer Temperature | Higher Temp→ Smaller Cryo-Radiator | <195 K | <175 K |
| Spectrometer Alignment | Warm Alignment→ Lower Integration Costs | Can be Aligned Warm | Cold Alignment Needed |
| Supported Cold Mass/Size (Relative) | Lower Mass/Size→ Smaller Cryo-Radiator | Mass = 0.1 Size = 1 | Mass = 1 Size = 1 |
| Total Relative Mass/Size | Smaller→Lower Mass | Mass = 1 Size = 2 | Mass = 1 Size = 1 |

In some embodiments of MISTiC, the spectrometer and detector and their corresponding thermal control elements are the largest and most power-intensive portions of the payload. The remaining elements of the MISTiC payload are listed below in Table 3, together with power and mass allocations, where the estimated totals are compared with the payload estimates for the A100 bus from ATK as an example of prior art approaches.

TABLE 3

Resource Requirements in an embodiment compatible with a Micro-Satellite Payload and comparison with prior art A100 payload

| MISTiC Instrument Element | Power (W) (Operate Mode) | Mass (Kg) |
| --- | --- | --- |
| Spectrometer Assembly | — | 4.5 Kg |
| Detector/Dewar/Cooler | 15 W (+5 control) | 1.2 Kg |
| On-Board Calibration Source | 1 | 0.2 |
| Spectral Data Handling Electronics | 8 | 1 |
| Payload Structure and Radiators | 3 | 3.5 |
| Miniature Scan Mirror/Control | 2 | 1.3 |
| Instrument Micro-controller | 1 | 0.2 |
| Instrument Power Converter | 5 | 0.1 |
| Payload Total | 40 W | 12 Kg |
| (Initial Design Margin) | (10 W) | (3 Kg) |
| A100 Payload Allocation | 50 W | 15 Kg |

In addition to using a highly efficient approach for the spectrometer, the on-board spectral data handling in embodiments of MISTiC employs an FPGA-based processing chain to minimize power needed for mitigation of transient gamma ray effects and sub-frame aggregation and formatting/encoding computations.

The fourth key attribute of the MISTiC approach is that embodiments of the disclosed method employ other observations to supplement the MISTiC observations, rather than adding functionality, cost and complexity to the MISTiC payloads. For infrared sounding spectroscopy, spectral channels in the LWIR window and 15 μm $CO_2$ emission bands can be used together with the MISTiC data to better-identify the presence of partial cloud-cover in a sounded region, to determine cloud phase, or to (better) observe ozone concentration. Specifically, the GOES-R ABI, MSG, and planned MTG multi-spectral imagers, as well as the SOUMI and JPSS-hosted VIIRS instruments, can provide high spatial resolution/multi-spectral observations of detailed cloud characteristics and $O_3$. The ABI can provide global refresh with 5-15 min refresh rates. The CrIS and IASI (and ongoing AIRS) high spectral resolution measurements in the LWIR provide information on the stratospheric temperature and humidity vertical profiles.

In turn, MISTiC can provide rapid refresh/high spatial resolution observations of CO and $N_2O$ in the troposphere that are superior in spatial resolution and refresh to those provided by other observing platforms, in addition to the vertical temperature and water vapor profile observations also provided by MISTiC.

Operational Concepts

Embodiments of MISTiC are compatible with launch as a secondary payload, attached to the Small Secondary Payload Adapter (8-inch bolt circle) on vehicles as small as the Minotaur IV with Standard Faring. Some of these embodiments can be used in an observing constellation, where the configuration of the constellation is tailored to the specific environmental data product set that is being sought. Some options for data product and for the constellation approach to support product acquisition are shown in Table 4 below. Listed are two example missions where three microsatellites are used to collect a triplet image set, and where spatial correlation measurements reveal layer-by-layer movements of the atmosphere. The table further includes a third mission that envisions either radiance assimilation, or vertical profile assimilation into an NWP model.

TABLE 4

Options for MISTiC Operational Concepts

| Mission Objective | Data Product Objective | Constellation Approach | # Payloads |
| --- | --- | --- | --- |
| Tropospheric Winds Observation (Prototype Operational Vertically Resolved Winds and Atmospheric State Observation | Fine Vertical Resolution 3-d Winds Products (Cloud and Moisture Motion Vector Winds) with Sounding Products | Observations by each of 3 instruments spaced by appx. 30 min. (same orbital plane | 9-12 |
| Rapid Refresh Temperature/Humidity Profile Observation | Separately Acquired Infrared Spectral Radiances, for | Independent observations by platforms in sun-synchronous orbits with | 8 |

TABLE 4-continued

Options for MISTiC Operational Concepts

| Mission Objective | Data Product Objective | Constellation Approach | # Payloads |
|---|---|---|---|
| (Prototype Operational Weather Observation) Secondary Transport Observation (e.g. supporting a GACM or PACE Primary NASA Mission) | Assimilation into Regional Weather Models Multi-level wind vector data co-incidentally collected with primary mission/trace chemical total column observations | nodal crossing times spaced by 90 minutes Observations by each of 3 instruments spaced by appx. 30 min (same orbital plane as primary payload) | 3 |

Figure 7:
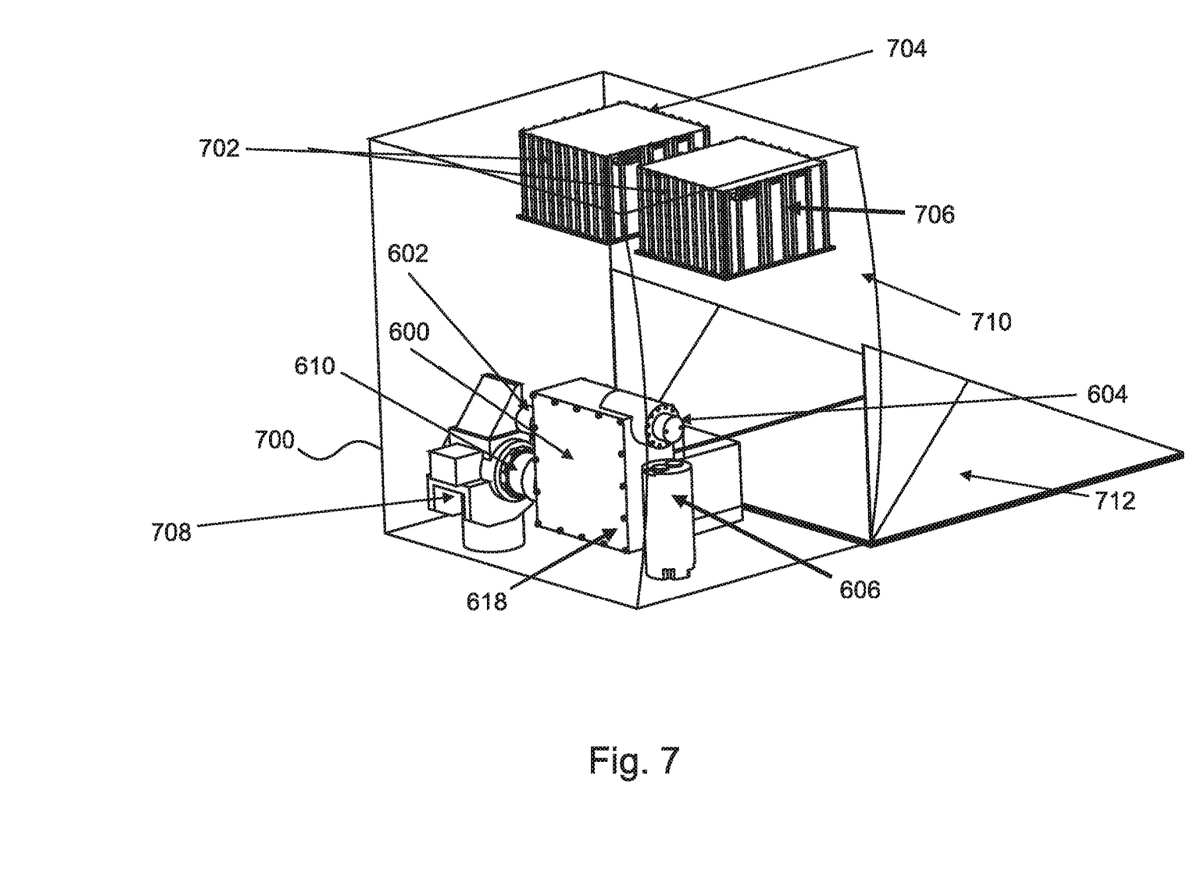
FIG. 7 is a perspective view drawn to scale of a complete MISTiC instrument in an embodiment, illustrating the primary components and showing the earth shield deployed.

Approximate launch costs of the entire constellation for some embodiments are much lower than the cost of one launch to geosynchronous orbit. FIG. 7 illustrates the major MISTiC payload elements in an embodiment that can be carried as a secondary payload having a volume of 20.75"× 18.75"×15", using the Small Secondary Payload Adapter Ring on a Minotaur IV vehicle (with Standard Faring). Features illustrated in FIG. 7 include the following:

Item Number Feature
700 NADIR
702 3U Electronics Boxes
704 Power Control and CMD/CNTRL FPNA Control Electronics
706 Cryo-cooler Electronics, Processor/Data Storage
708 Scan Mirror & Calibration Assembly
710 Radiator Face
712 Earth Shield As another option, a DMSP launch can be used to launch one or more MISTiC satellites carried aboard its ESPA ring. Overall launch and mission costs depend on several factors, including the types of observations to be made (such as Winds Measurement, or Rapidly Refreshed Atmospheric State). The first (and third) options are most amenable to launching multiple MISTiC—bearing spacecraft into the same orbital plane, to be separated into the wind-observation formation at low energy cost. The second mission type requires multiple orbital planes, and orbiting the full constellation in embodiments requires a combination of multiple launches, as well as passive and active orbital plane changes, to fully deploy.

3.0 Comparative Technology Assessment

There are several different approaches to a comparative assessment of MISTiC against other technologies. One approach is to compare small MWIR spectrometer implementations, as shown in Table 2 above. A second type of comparison is at the observation level, where the MISTiC approach using a constellation of smaller low earth orbit satellites for rapidly refreshed temperature and water vapor vertical profile observations is compared with geosynchronous implementation of the same observation as planned for HES. Table 5 shows this comparison.

In these examples, different orbits lead to different types of earth coverage. A single geosynchronous instrument only views a disk within 60 degrees local zenith angle, whereas a MISTiC device in low earth orbit provides more complete (near-global) coverage (with modest precessing coverage gaps near the equator). It is possible to make an approximate comparison between the resources required for (near) global coverage at similar rates. The resources required for MISTiC are at least an order of magnitude smaller than those needed for HES for comparable coverage.

TABLE 5

Comparative Estimates for Instruments for Tropospheric Wind Measurements

| Instrument | Power | Size (cm) | Mass | Wind Levels in Troposphere (>450 mb) | Atmospheric State Measured? | Orbit and # Platforms |
|---|---|---|---|---|---|---|
| MISTiC | 50 W | 15 × 25 × 25 | 15 | ~10 | YES | LEO (12) |
| HES | 550 W | 170 × 170 × 150 | 315 | ~10 | YES | GEO (6) |
| Hybrid Wind LIDAR (est) | 750 W | 150 ×150 ×100 | 400 | 10-15 | NO | LEO (4) |
| Cube-Sat With UncooledLWIR Detector- (est) | 12 W | 10 × 10 × 30 | 2-3 | ~2 | NO | LEO (~24) |

Those skilled in the art will appreciate that aspects of the invention that reduce the optical system size and cooling requirements for a thermal infrared imaging spectrometer are also applicable to other hyperspectral imaging systems that are designed for airborne, space, and/or ground applications.

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

This specification is not intended to be exhaustive. Although the present application is shown in a limited number of forms, the scope of the invention is not limited to just these forms, but is amenable to various changes and modifications without departing from the spirit thereof. One or ordinary skill in the art should appreciate after learning the teachings related to the claimed subject matter contained in the foregoing description that many modifications and variations are possible in light of this disclosure. Accordingly, the claimed subject matter includes any combination of the above-described elements in all possible variations thereof, unless otherwise indicated herein or otherwise clearly contradicted by context. In particular, the limitations presented in dependent claims below can be combined with their corresponding independent claims in any number and in any order without departing from the scope of this disclosure, unless the dependent claims are logically incompatible with each other.

What is claimed is:

1. A device suitable for making infrared atmospheric measurements, the device comprising:
    an avalanche infrared photodiode array;
    a cryo-cooler configured to cool the photodiode array;
    a spectrometer having an Offner architecture, said spectrometer including a grating and a refractive element proximal to the grating;
    an optical and self-emission baffle; and
    a two-zone passive thermal radiator having a first zone configured to cool the baffle while in orbit and a second zone configured to cool the spectrometer while in orbit.

2. The device of claim 1, wherein the cryo-cooler is configured to cool the photodiode array to a temperature that is between 75K and 100K.

3. The device of claim 2, wherein the cryo-cooler is able to cool the photodiode to a temperature below 100K while consuming less than 15 W of power.

4. The device of claim 1, wherein the cryo-cooler is an NGST miniature pulse-tube cooler that has a specific cooling power of at least 20 W/W at 100K.

5. The device of claim 1, wherein the first zone of the two-zone radiator is able to cool the baffle to a temperature that is between 175K and 195K.

6. The device of claim 1, wherein the spectrometer is limited to detecting infrared radiation in the range of 1950 $cm^{-1}$ to 2450 $cm^{-1}$.

7. The device of claim 1, wherein the spectrometer is configured to detect water vapor absorption lines in the range of 1950-2325 $cm^{-1}$.

8. The device of claim 1, wherein the spectrometer has a minimum resolution of less than 2.3 $cm^{-1}$.

9. The device of claim 1, wherein the spectrometer has a radiometric sensitivity threshold of less than 200 mK.

10. The device of claim 1, wherein the device has a total weight of less than 12 kg.

11. The device of claim 1, wherein the device has a total power consumption requirement of less than 40 W.

12. The device of claim 1, further comprising an on-board spectral data handling system that employs an FPGA-based processing chain.

13. A method of making hyperspectral soundings of the earth's atmosphere from a constellation of earth satellites, the method comprising:
    deploying a plurality of satellites in a constellation of orbits surrounding the earth, wherein a device as described in claim 1 is included with each of the satellites; and
    obtaining from the devices cooperative distributed infrared sensing measurements of atmospheric phenomena.

14. The method of claim 13, wherein the satellites are deployed in low earth orbit at an altitude of approximately 705 km above the earth's surface.

15. The method of claim 13, wherein the constellation is able to make observations of a region that are repeated every 90 minutes.

16. The method of claim 13, wherein the constellation is able to make repeated observations of a region with a repetition interval of less than fifteen minutes.

17. The method of claim 13, wherein observations obtained from the constellation are provided together with observations obtained from other devices as input for at least one of atmospheric modeling and weather forecasting.

* * * * *